US009652590B2

(12) United States Patent
Yeager (10) Patent No.: US 9,652,590 B2
(45) Date of Patent: May 16, 2017

(54) SYSTEM AND METHOD TO SIMULATE MAINTENANCE OF A DEVICE

(71) Applicant: GENERAL ELECTRIC COMPANY, Schenectady, NY (US)

(72) Inventor: Linda Kay Yeager, Madison, WI (US)

(73) Assignee: General Electric Company, Schenectady, NY (US)

( * ) Notice: Subject to any disclaimer, the term of this patent is extended or adjusted under 35 U.S.C. 154(b) by 348 days.

(21) Appl. No.: 14/315,361

(22) Filed: Jun. 26, 2014

(65) Prior Publication Data

US 2015/0379221 A1    Dec. 31, 2015

(51) Int. Cl.
| | |
|---|---|
| G06F 15/00 | (2006.01) |
| G06F 13/00 | (2006.01) |
| G06F 19/00 | (2011.01) |

(52) U.S. Cl.
CPC ...... *G06F 19/3406* (2013.01); *G06F 19/3412* (2013.01)

(58) Field of Classification Search
CPC .............................. G09B 23/281; A61B 17/02
USPC .................. 715/763–765, 740–745, 771
See application file for complete search history.

(56) References Cited

U.S. PATENT DOCUMENTS

| | | | |
|---|---|---|---|
| 5,791,908 A | 8/1998 | Gillio | |
| 6,283,763 B1 | 9/2001 | Matsuzaki et al. | |
| 6,449,103 B1 | 9/2002 | Charles | |
| 7,657,566 B2 | 2/2010 | Mathavu et al. | |
| 7,792,565 B2 | 9/2010 | Vining | |
| 7,984,659 B2 | 7/2011 | Fujimoto et al. | |
| 8,184,773 B2 | 5/2012 | Cheng et al. | |
| 8,235,726 B2 | 8/2012 | Hostettler et al. | |
| 8,423,135 B2 | 4/2013 | Doerr et al. | |
| 8,439,688 B2 | 5/2013 | Wilkins | |
| 8,473,852 B2 | 6/2013 | Russell | |
| 8,500,451 B2 | 8/2013 | Bronstein et al. | |
| 8,600,551 B2 | 12/2013 | Itkowitz et al. | |
| 8,690,325 B1 | 4/2014 | Straus et al. | |
| 8,721,344 B2 | 5/2014 | Marmaropoulos et al. | |
| 2005/0174235 A1 | 8/2005 | Davis et al. | |
| 2014/0005484 A1* | 1/2014 | Charles ................... | A61B 17/02 600/201 |
| 2015/0018622 A1* | 1/2015 | Tesar ....................... | A61B 1/05 600/202 |
| 2015/0079565 A1* | 3/2015 | Miller ................... | G09B 23/281 434/252 |
| 2015/0272694 A1* | 10/2015 | Charles .............. | A61B 19/5212 600/202 |

* cited by examiner

*Primary Examiner* — Kevin Nguyen (57) ABSTRACT

A system and method to virtually simulate maintenance of a medical device located in a defined space by a user is provided. The system can include a main interactive touchscreen; and a central controller connected in communication with the touchscreen monitor. The central controller can execute a series of computer-readable program instructions to perform comparing a detection of contact by the user at the touchscreen relative to a graphic representation of a virtual view of the component of the medical device relative to one of a series of predefined tasks associated with a maintenance procedure of the medical device stored in a database, and generating a display illustrative of a completion of the maintenance procedure upon calculating a completion of each of the plurality of predefined tasks.

20 Claims, 6 Drawing Sheets

SYSTEM AND METHOD TO SIMULATE MAINTENANCE OF A DEVICE

FIELD OF DISCLOSURE

The present disclosure relates to a simulation engine, and more particularly to systems and methods to simulate service and maintenance on a medical device.

BACKGROUND

The statements in this section merely provide background information related to the disclosure and may not constitute prior art.

The need to teach equipment service technicians on how to operate, repair, and maintain medical devices has traditionally relied on technical training exercises performed on actual medical equipment. A drawback of such technical training exercises is high upfront cost for the availability of very expensive equipment having associated complex and expensive installation support infrastructure. As an alternative to reduce the expense of training on actual medical devices, others have recorded videos to teach user about a specific technical training to service or maintain on medical devices. Such videos can be stored and distributed on portable storage mediums (e.g., CDs, DVDs, etc.) to be uploaded for presentation on computer. A drawback of such recorded video training is that the user is not provided with any hands-on interaction to simulate work on the actual device.

BRIEF SUMMARY

In view of the above, there is a need for systems, methods, and computer program products which teach equipment service technicians using hands-on interaction to simulate how to operate, repair, and maintain medical devices. The above-mentioned needs are addressed by the subject matter described herein and will be understood in the following specification.

According to one aspect, a system to virtually simulate maintenance of a medical device located in a defined space by a user is provided. The system can include a main interactive touchscreen; and a central controller connected in communication with the touchscreen monitor. The central controller can execute a series of computer-readable program instructions to perform comparing a detection of contact by the user at the touchscreen relative to a graphic representation of a virtual view of the component of the medical device relative to one of a series of predefined tasks associated with a maintenance procedure of the medical device stored in a database, and generating a display illustrative of a completion of the maintenance procedure upon calculating a completion of each of the plurality of predefined tasks.

According to another aspect, a method to virtually simulate maintenance of a medical device located in a defined space by a user is provided. The method can include the steps of: generating a graphic image by computer processor at a touchscreen representative of a component of the medical device; comparing a detection of contact by the user at the touchscreen relative to the graphic representation of a virtual view of the component of the medical device relative to one of a plurality of predefined tasks associated with a maintenance procedure of the medical device as stored in a database, and generating an output in electronic format illustrative of a completion of the maintenance procedure upon calculating a completion of each of the plurality of predefined tasks.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description in conjunction with the drawings in which reference numerals indicate identical or functionally similar elements.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. The term user and/or the plural form of this term is used to generally refer to those persons capable of accessing, using, or benefiting from the present disclosure. As used herein, when the phrase "at least" is used, it is open-ended in the same manner as the term "comprising" is open ended.

Figure 1:
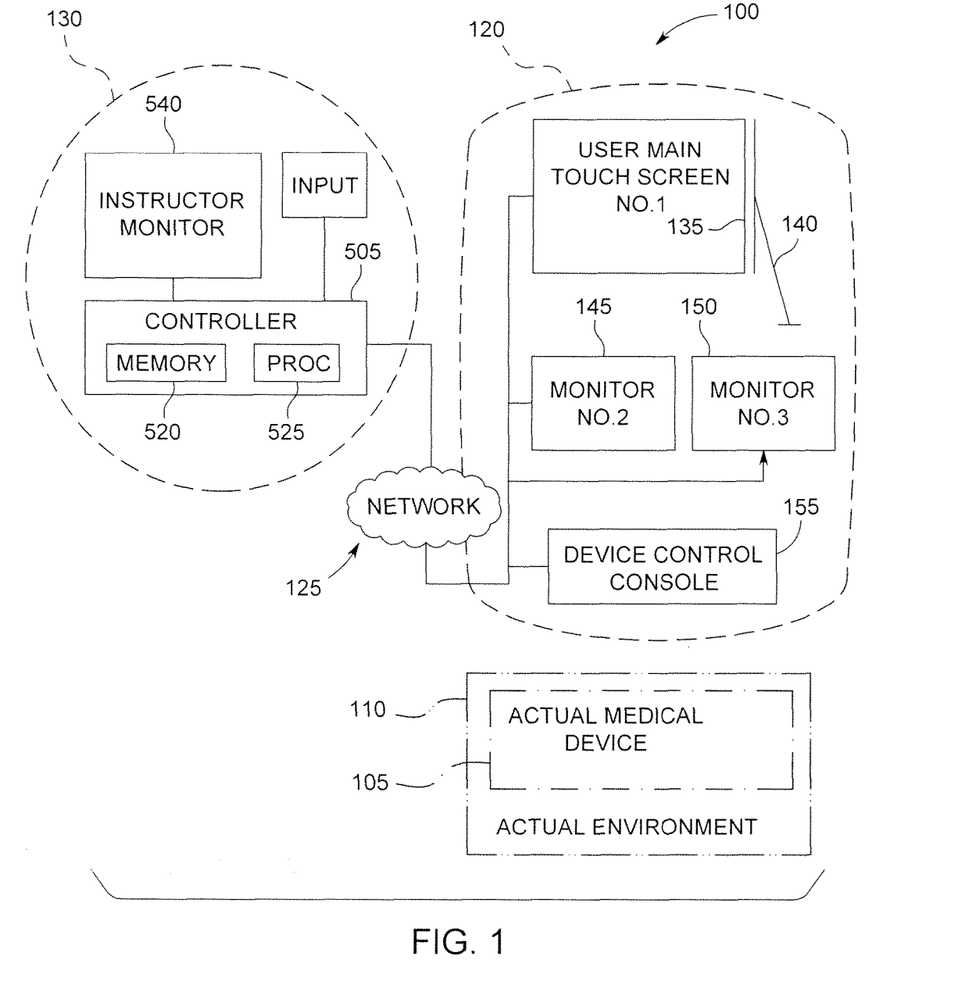
FIG. 1 shows a schematic block diagram of an example of a system to in accordance to the subject matter described herein.

Referring to FIG. 1, a diagram of example of a system 100 is shown to virtually simulate for a user the maintenance or other related tasks to be performed by a user on an actual medical device (shown in dashed line for sake of description, but not part of system) located in a defined environment or space. The system 100 can be generally configured or operable to simulate maintenance by generating or creating a three-dimensional, virtual visualization and interaction with medical device 105 in the actual medical device environment 110 (shown in dashed line for sake of description). Further, the system 100 can provide the ability for the user to operationally interact with generally the same software or hardware that would be found on actual medical device 105.

The example of the system 100 can include multiple user training stations (hereinafter referred to as "STS") 120 connected in communication over a network 125 with an instructor operating station (herein after referred to as "IOS") 130. An example of each STS 120 can include a main, pressure-sensitive, unlimited-touch interactive touchscreen 135 on a tilting mount 140, along with monitors 145, 150 (e.g., can also be multi-touch sensitive displays, or conventional LCD monitors or the like) supported by articulating mounts (not shown). The STS 120 can further include a shelf (not shown) holding a medical device control console 155 including miscellaneous control peripherals (e.g., keyboard, toggle switches, etc.) that would be associated with the actual medical device 105, and an un-interrupted Power Supply (UPS) (not shown).

The main, interactive touchscreen 135 is generally an interactive user interface operable to detect or track multi-contact gestures by the user (e.g., finger or hand movements) (herein "gestures") at the main interactive touchscreen 135, in a manner that can replicate human actions or motions of a service technician in actual performance of an assigned task on actual medical device 105 in the actual medical device environment 110. In tracking these gestures, the system 100 allows the user to interact as if they were performing tasks on the actual medical device 105. The ability to track or detect gestures relative to graphic representations (herein icons) on the main interactive touchscreen 135 provides the user with virtual, kinesthetic interactions that mirror actual performance of tasks on the actual medical device 105 in the actual medical device environment 110, enhancing the realism of training and improving the user's experience and outcome (i.e. knowledge and skills transfer).

Each of the touchscreens or monitors 135, 145, 150 can display icons or graphics in a 3D environment, and can be reconfigured to display several different views of the actual medical device 105 during run-time. The primary visualization of the simulated performance of tasks to train the user in performing maintenance or service on the actual medical device 105 can be at the main interactive touchscreen 135 of the STS 120. This main interactive touchscreen 135 allows the user to manipulate physics-based objects via multi-touch and with pressure-sensitive technology, allowing the user to virtually interact with equipment components of the actual medical device 105 with a familiar and realistic look and feel. Visual, graphic objects or icons or representations on the main touchscreen 135 react to the number of user fingers in contact with the main touchscreen 135, the force of which the user pushes against the main touchscreen 135, and the graphic representations simulation of the of the actual weight of the component of the actual medical 105 itself. The other displays 145, 150 can be used to interact with the control console 155, and virtual simulation of any portions of the actual medical device 105 that requires special viewing.

Figure 2:
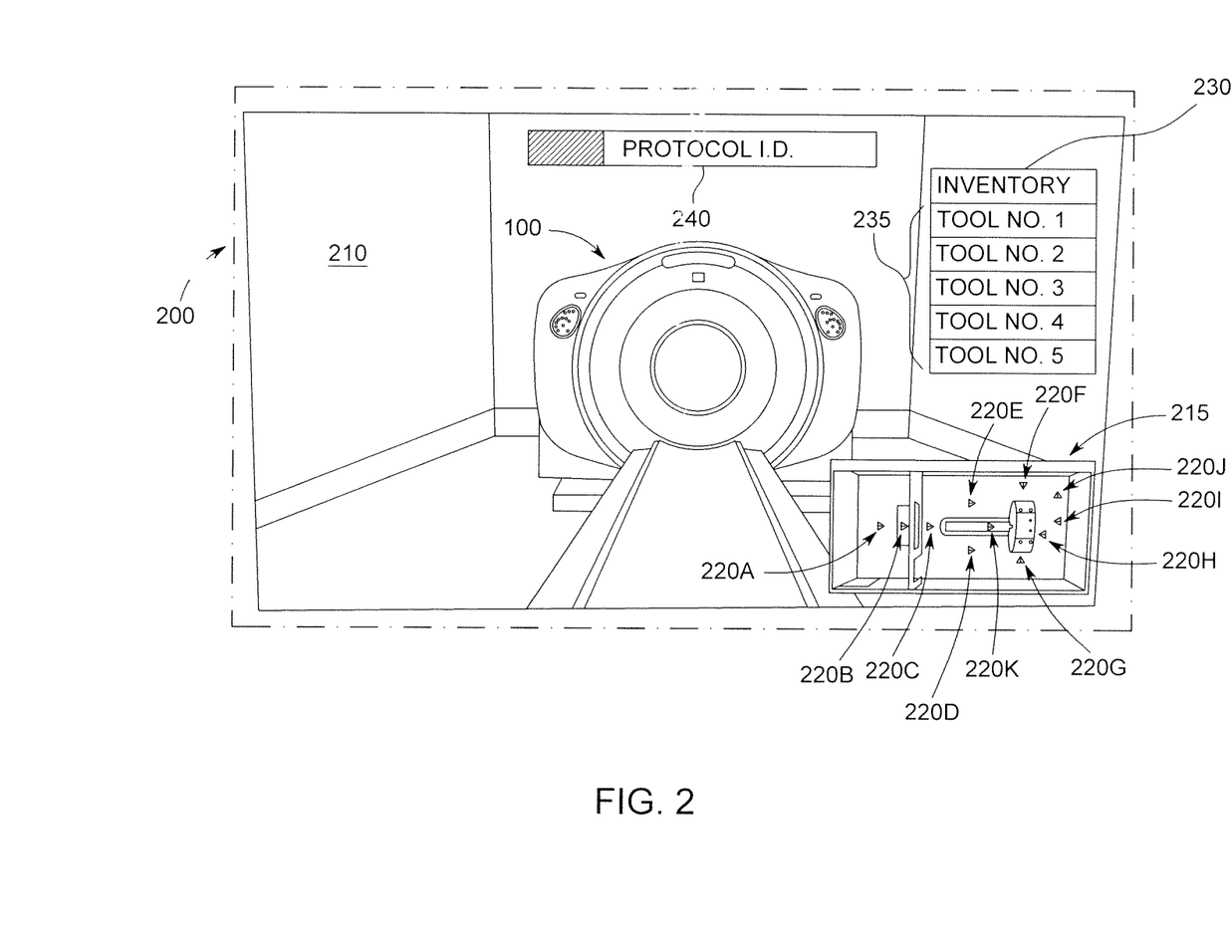
FIG. 2 shows an illustration of a first example of an interactive graphic user interface generated by the system of FIG. 1 in accordance with the subject matter described herein.

FIG. 2 illustrates an example of a graphic user interface or display 200 generated by the system 100 for visualization to the user at the main interactive touchscreen 135 of the STS 120. The graphic user interface 200 can be in the form of a network interface or graphic user interface (GUI) to exchange data, instructions, or illustrations via the user main interactive touchscreen 135, for example. The graphic user interface 200 can include a first virtual view 205 illustrative of (the perspective of the view can vary) 205 of the overall actual medical device 105 relative to a virtual view 210 of the actual environment 110. The graphic user interface 200 can further include another virtual image 215 of the actual medical device 105 in the environment 110, the image 215 including a series of graphic icons (shown as arrows and reference 220a-220j) each associated with different predefined user locations and viewpoints to simulate performance the maintenance or service procedure to the medical device relative to the defined space, for selection with a gesture at the touchscreen 135 by the user. Virtual image 215 is shown as a picture in picture relative to the graphic user interface 200, but the illustration of the image 214 relative to the view 205 can vary (e.g., side by side, etc., window type panes, etc.).

In this example, in response to user selection of (via detected gesture at the touchscreen 135): graphic icon 220a triggers generation of a virtual view of the control console in a control room; graphic icon 220b triggers generation of a virtual view through a window of the control room to the medical device 105; graphic icon 220c triggers generation of the virtual view of the medical device 105 as shown by virtual view 205; graphic icons 220d, 220e triggers generation of the virtual view of a front view to either side of the medical device; graphic icons 220f, 220g triggers generation of the virtual view of respective side panels of the medical device 105; graphic icons 220h, 220i triggers virtuals views to different locations of rear views of the medical device 105; graphic icon 220j triggers generation of the virtual view to a related accessory or local control panel in the environment 110; and graphic icon 220k triggers generation of the detailed virtual of the front of the enclosure of the medical device 105. The illustrated icons 220a-220k are predefined to perform miscellaneous procedures or protocols to the medical device 105 shown (a CT scanner). Although certain graphic icons associated with predefined virtual views of the medical device 105 are shown, the number of icons associated with locations and perspective views of the medical device can vary to provide the proper experience to the user in performance of the predefined procedures or protocols for the type of medical device 105.

FIG. 2 further includes a graphic illustration of a tool box 230 (labelled inventory) with a dropdown menu of a selection of tools 235 predefined to perform the selected procedure or protocol on the medical device 105. The system asks the user to select the proper tool 235 from the toolbox 230 in performing each assigned task of the selected procedure or protocol. Graphic illustration 240 shows a visualization of a percentage progress by the user through completion of the selected procedure or protocol. Graphic icon 245 prompts the user to select from multiple types of modes of instruction or simulation (e.g., semi-guided, etc.) that is discussed later. The illustration 240 of the predefined set of tools associated with completing the respective maintenance process (as visually illustrated at reference 240) on the medical device 105. The system can identify the selection of one of the predefined set of tools per interaction of the gesture by the user at the visual illustration 235 of one of the selection of tools as shown on the touchscreen 135, and compare this identified selection of tool relative to a predefined tool to perform the applicable task of selected procedure or process being simulated by the system 100. The identified selection of the tool can be graphically illustrated by highlighting or other marking to visually illustrate the selection on the touchscreen 135 to the user. The system 100 includes programming that can be associated with a particular procedure or protocol file, the programming representative of a unique, predefined tool to perform a predefined task in completing the respective procedure.

Figure 3:
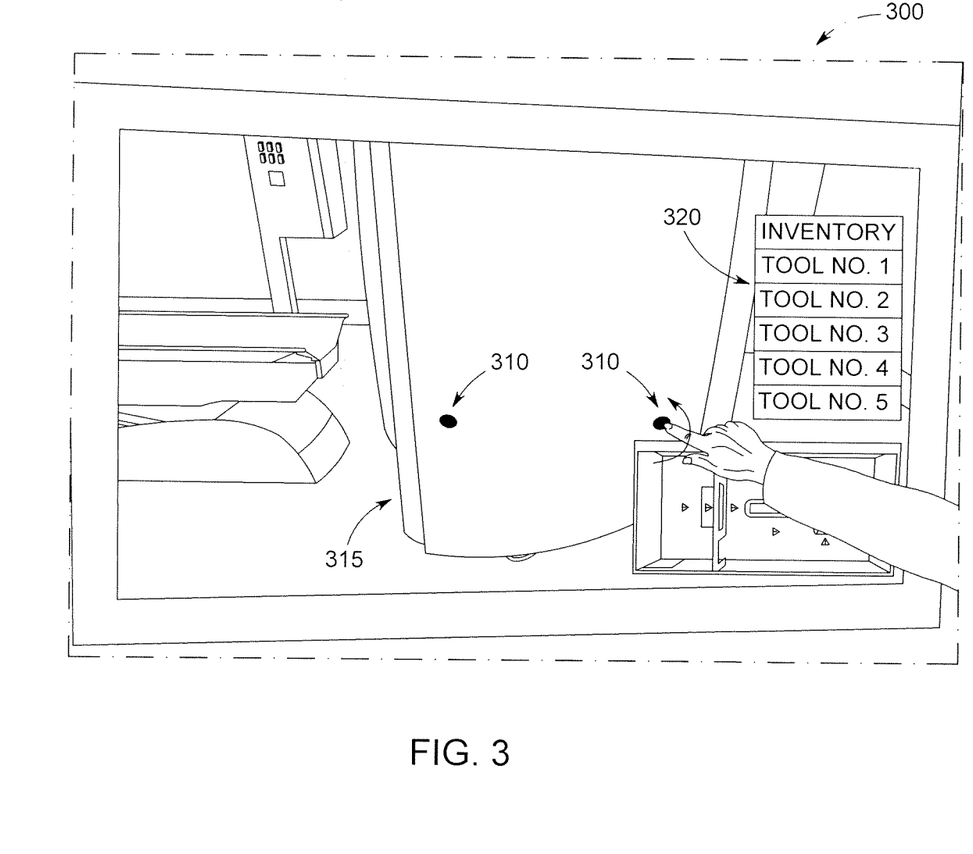
FIG. 3 shows an illustration of a second example of an interactive graphic user interface generated by the system of FIG. 1 in accordance with the subject matter described herein.

FIG. 3 further illustrates another example of a graphic user interface or display 300 of the side component of the medical device 105 generated in response to detecting the user gesture (e.g., finger contact) at graphic icon 220g in FIG. 2. The user may be prompted by a graphic representation of an instruction to the user as generated by the system 100 to select this the graphic user interface 300 to complete a certain predefined task of the selected procedure. The graphic user interface 300 includes a graphic representation 305 of a predefined component (i.e., side panel 315 of the CT scanner) affected by the predefined task (e.g., remove side panel 315) as part of completion of the predefined procedure simulated by the system 100. The graphic user interface 300 further includes a graphic representation 310 of a set of bolts that per the procedure or protocol is to be removed by the user so as to remove the side panel 315 and access certain components (See FIG. 4—discussed later) of the medical device 105. The system 100 can be programmed to detect a certain gesture (e.g., circular motion of by finger contact at the graphic representation 310 of the bolt in the predefined direction correct for removal of the actual bolt from the side panel 315 of the actual medical device 105 in the field). Without detecting correct selection of the tool 320 in combination with the view and correct gesture at the touchscreen 135, the system 100 will not indicate that the predefined task is completed and prevent the user from proceeding to the next task of the protocol.

Figure 4:
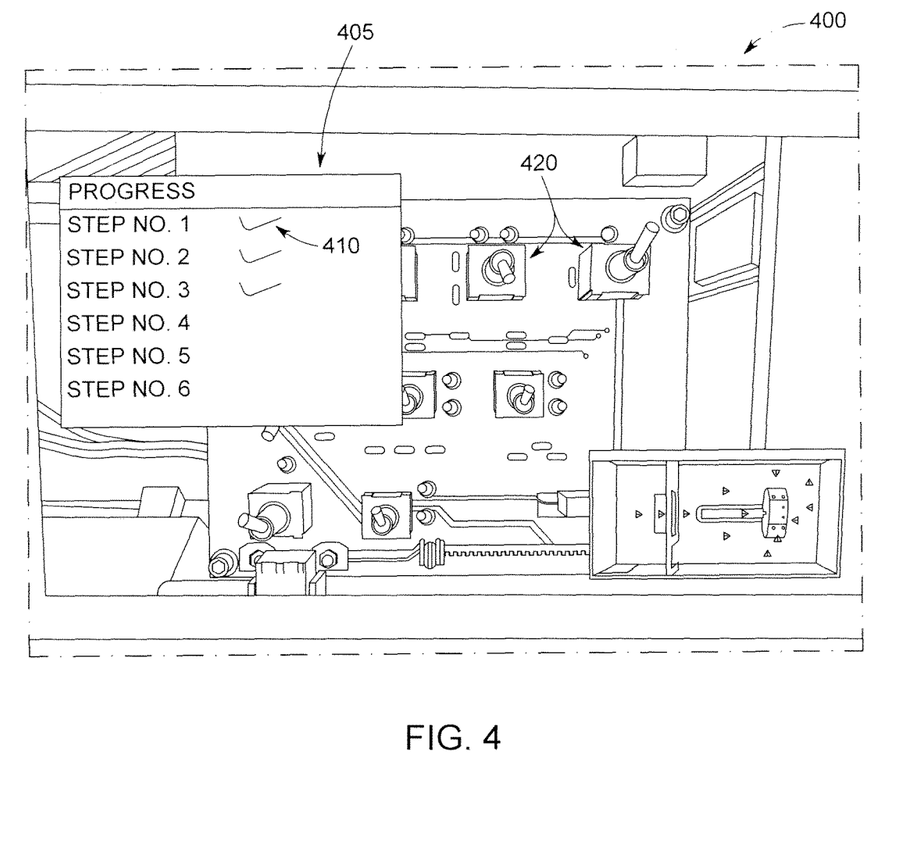
FIG. 4 shows an illustration of a third example of an interactive graphic user interface generated by the system of FIG. 1 in accordance with the subject matter described herein.

FIG. 4 illustrates a graphic user interface or display 400 of predefined components to be viewable with completion of the task to remove the side panel (see reference 315 of FIG. 3) from the medical device (see reference 105 of FIG. 1), the graphic user interface 400 generated in response to detection of gestures at the graphic representations 310 associated with removal of the bolts and gesture to lift the virtual image of the side panel, the gestures as detected at the touchscreen 135 as partially described above with reference to FIG. 3. the graphic user interface 400 further includes a graphic representation 405 listing the multiple tasks to completed to perform the selected procedure or protocol, and a status of progress or completion (e.g., illustrated by graphic icons 410 of check marks). This graphic representation 405 can be generated by the system 100 in response to an instruction from the user associated with detecting the gesture relative to the training mode. Per graphic representation 405, the next tasks of the selected protocol to complete include turning several toggle switches from the ON to the OFF positions. the graphic user interface 400 includes graphic representations 420 of at least one of the toggle switches of the medical device 105 to be actuated from the ON to the OFF position before proceeding to the next task.

Referring back to FIG. 1, the IOS 130 provides the instructor with an ability to deliver electronic-based curriculum content for the transfer of concepts and tasks associated with a selected procedure or protocol to the user. In the delivery of such curriculum from the instructor to the user, the IOS 130 can comprise a controller 505 connected in communication over the network 125 with each of the STS(s) 120. With such connection of the IOS 130 over the network 125 with each STS 120, the instructor can view on the IOS 130 each of the tasks that each user is assigned and performing. More specifically, the IOS 130 can includes a graphic illustration 510 to the instructor that provides a constant view to each user's progress to determine if each assigned task is being completed successfully, indicating acquisition of the knowledge and skill to perform the task on the actual medical device 105. Additionally, if a user is encountering difficulty in task mastery, the IOS 130 can include a graphic illustration 515 of an alert to make the instructor aware that intervention is required, with data as to what specific areas are proving difficult. The IOS 130 can then display the user's accomplishment history to allow the instructor to determine how best to remediate the difficulty. The ability of the system 100 to track (via gestures at the touchscreen 135) progress (see reference 510) and generate alerts (see reference 515) as the user progresses through the predefined procedure combined with the instructors ability via the IOS 130 to provide the user with coaching and remediation can provide significant improvement in the learning or training outcome of the user.

The controller 505 generally operates to receive, process, and convey information to and from the STS 120 and other components of the system 200. The example of the controller 505 generally includes a memory 520 having a series of computer readable program instructions for execution by a computer processor 525 in executing the simulation of the procedure or protocol to the user of the system 100.

The example memory 520 can include a tangible, non-transitory, computer readable storage medium of varying type generally operable to store electronic formatted data or information and program instructions accessible and readable by the computer processor 525. In certain examples, the memory 520 can be accessible by an external computing device 530 via the network 125.

The computer-readable instructions can comprise a programming code for execution by the computer processor 525. The programming code can be embodied in software stored on the memory 505 independent of or in combination with software embodied in firmware or dedicated hardware. The computer readable storage medium (also referred to as a computer program product) can be tangible, non-transitory, and include volatile and non-volatile, and removable and non-removable media for storage of electronic-formatted information such as computer readable program instructions or modules of instructions, data, etc. that may be stand-alone or as part of the controller 505. As used herein, the term tangible, non-transitory computer readable storage medium can be expressly defined to include any type of computer readable storage device and/or storage disk and to exclude propagating signal media and to exclude transmission media. As used herein, "tangible computer readable storage medium" and "tangible machine readable storage medium" can be used interchangeably. Examples of memory 505 can include, but are not limited to, random access memory (RAM), read only memory (ROM), Synchronous Dynamic Random Access Memory (SDRAM), Dynamic Random Access Memory (DRAM), EEPROM, flash memory, a cache, compact disc (CD), digital versatile disc (DVD) or other optical storage, magnetic cassettes, magnetic tape, magnetic disk storage or other magnetic storage devices, a hard drive, a flash memory, or any other medium which can be used to store the desired electronic format of information or program instructions for a duration and which can be accessed by the computer processor 525 or at least a portion of the controller 505.

The example computer processor 525 can include hardware to execute one or more tasks as defined by the computer readable program instructions. The example computer processor 525 can also process data received at the system 100 and generates output (e.g., visual illustrations) that can be provided to one or more of the IOS 130 and the STS 120. For example, the example computer processor 525 can take an instructor annotation received via the IOS 130 and can generate a report associated with the progress of the user. The computer processor 525 can be, for example, part of a server, a laptop or desktop, a mobile device (e.g., a cell phone, a smart phone, a tablet such as an IPAD™), a personal digital assistant (PDA), an Internet appliance, or any other type of computing device. For example, the computer processor 505 can be implemented by one or more integrated circuits, logic circuits, microprocessors or controllers from any desired family or manufacturer.

Memory 520 and computer processor 525 as referred to herein can be stand-alone or integrally constructed as part of various programmable computing devices of various types, including for example a cache, a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like and any combination thereof operable to execute the instructions associated with implementing the method (discussed later) of the subject matter described herein.

The controller 505 and external computing device 530 as referenced herein can include: a mobile telephone; a computer such as a desktop or laptop type; a Personal Digital Assistant (PDA) or mobile phone; a notebook, tablet or other mobile computing device; or the like and any combination thereof. The subject matter of this description may be implemented as stand-alone or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

The network 125 can facilitates transmission of electronic data within and/or among one or more STSs 120 and IOS 130. The example network 125 can be a wired interface (e.g., a data bus, a Universal Serial Bus (USB 2.0 or 3.0) connection, etc.) and/or a wireless interface (e.g., radio frequency, infrared, optical, near field communication (NFC), etc.), a wide area network (WAN); a local area network (LAN); the Internet; a cloud-based computing infrastructure of computers, routers, servers, gateways, etc.; or any combination thereof associated therewith that allows the system 100 or portion thereof to communicate with one or more STSs 120, the IOS 130, and external computing devices 530.

With respect to the example of the network including a cloud-based infrastructure, the system 100 can share information via web-based applications, cloud storage and cloud services. For example, a Web-based portal may be used to facilitate access to information, etc. The STS 120 and IOS 130 can illustrate the Web-based portal as a central interface to access information and applications, and data may be viewed through the Web-based portal or viewer, for example. Additionally, data may be manipulated and propagated using the Web-based portal, for example. The Web-based portal can be accessible locally (e.g., in an office) and/or remotely (e.g., via the Internet and/or other private network or connection), for example.

As illustrated in FIG. 1, the IOS 130 can further include additional instructor input devices 540 operable to permit the user to enter data and instructions to the system 100. such as a keyboard, additional touch-screens, a mouse, a trackball, a track pad, a camera or optical barcode recognition, microphone or other means of voice command and recognition, etc. or combination thereof used to communicate an instruction or data from the instructor to the system 100. The IOS 130 can further include instructor output devices 540 to provide (e.g., visualizations, audible illustrations, and other sensory feedback in the form of vibrations, heat versus cold, etc.) to the user. Examples of output devices 540 can include a monitor (e.g., liquid crystal display (LCD), plasma display, cathode ray tube (CRT), etc.), light emitting diodes (LEDs), a touch-screen, a printer, a speaker, or other conventional display device or combination thereof. The output devices 540 of the illustrated example, thus, can typically include a graphics driver card, a graphics driver chip or a graphics driver processor to create the described displays 200, 300 and 400.

Having provided an embodiment of one construction of the system 100 as shown in FIG. 1 in accordance with above-description as well as various displays (see FIGS. 2-4) generated by the system 100, the following is a description of an embodiment of a method 600 (See FIG. 5) to operate the system 100 in accordance with the subject matter described herein 100. It should also be understood that the sequence of the acts or steps of the method 600 as discussed in the foregoing description can vary. Also, it should be understood that the method 600 may not require each act or step in the foregoing description, or may include additional acts or steps not disclosed herein. It should also be understood that one or more of the steps of the method 600 can be represented by one or more computer program modules of computer-readable program instructions stored in the system 100. As mentioned above, the method 600 of FIG. 5 can be implemented using coded instructions (e.g., computer and/or machine readable instructions). The terms module and component as referenced herein can generally represent program code or instructions that causes specified tasks when executed on the computer processor 525. The program code can be stored in one or more computer readable mediums.

Prior to providing training to users with the system 100, it should be understood that a job duty task analysis be recorded as files of programmed instructions into the system 100, each file identifying a sequence of predefined tasks of a particular maintenance or service procedure to train the user of the system 100. The identified tasks can be evaluated and scored for a list of predefined criteria to be saved and stored with an information file for the respective task or overall procedure, including difficulty to perform the task, frequency of the task, difficult to learn, and the level of previous training. Based on this evaluation and scoring, the overall procedure that includes the task can be assigned a level of training (e.g., 1, 2, 3, and 4) to be saved and stored with the respective file of programmed information of the respective procedure.

Also prior to providing training with the system 100, the system 100 can be provided or stored with computer readable computer program instructions operable to identify and translate predefined gestures detected at the interactive touchscreen 135 to compare with stored parameters for the identified actions by the user to perform the tasks of the respective procedure. In one example, the programming of such gesture recognitions by the system 100 can be designed for a multi-level, interactive touchscreen 135 environment. The gestures to be recognized in combination with location of the generated icons and graphics described in the displays 200, 300, 400 for illustration on the interactive touchscreen 135 such that the user experience is generally identical or similar to the actual actions to complete the task on an actual medical device 110. This approach provides exceptional realism during the removing/replacing of parts, performing calibrations and removing covers from the actual medical device 110. The system 100 can be programmed to identify the gestures at the touchscreen 135 based on advanced analysis of the movement physics to replicate actions to perform the procedure on the actual medical device 110. Additionally, combining 3D virtualization, learning aides and automated assessment tools can provide the ability for the user to experience successful learning outcomes usually only resulting from traditional training employing actual equipment solutions. The system can be programmed with Troubleshooting scenarios that allows the instructor to show actual problems in the field that could not be created with damaging the actual medical devices 110.

Figure 5:
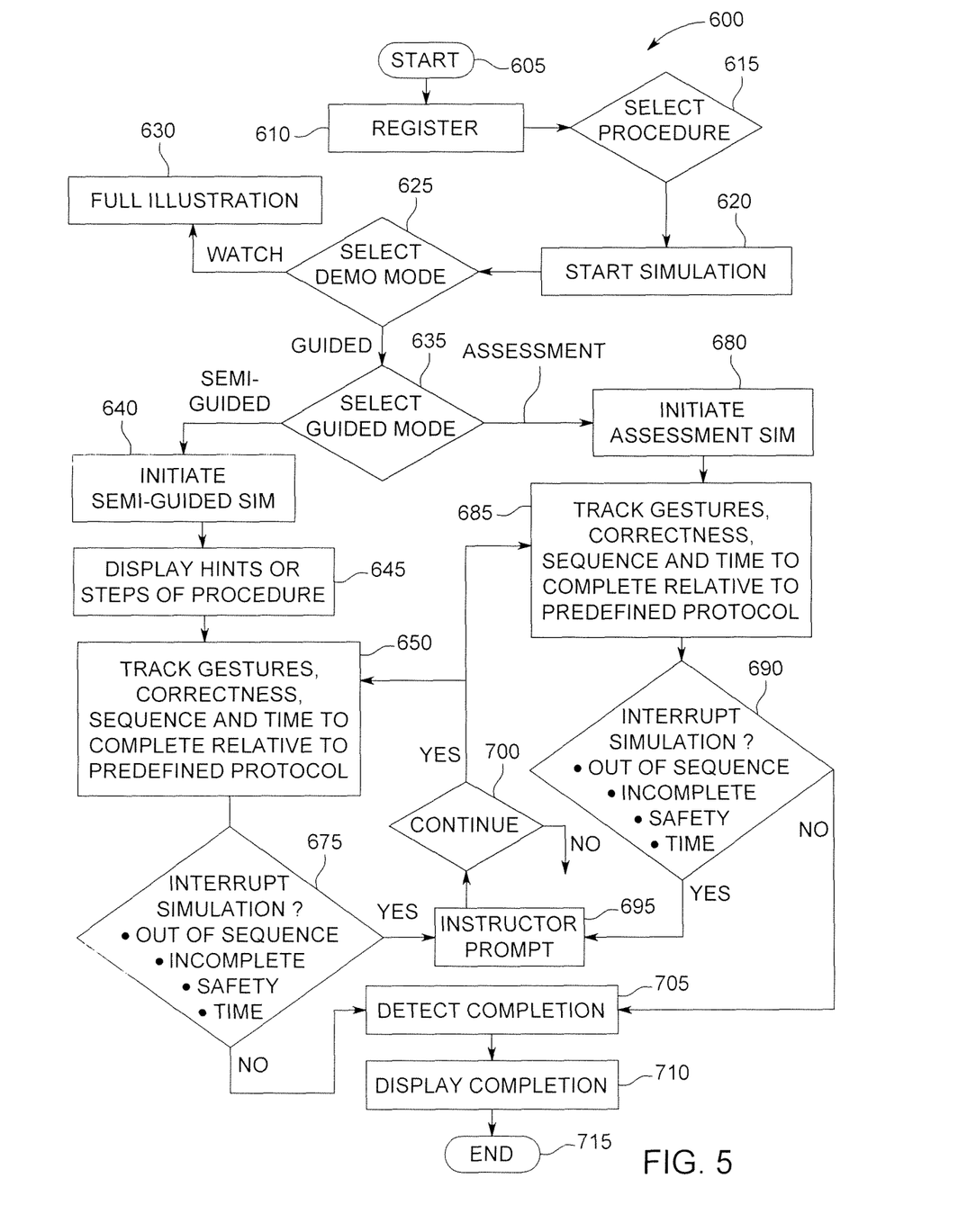
FIG. 5 illustrates a schematic flow diagram of an example of a method of operating the system of FIG. 1, according to the subject matter described herein.

Step 605 of the method 600 can include a start of operation of the system 100. Step 610 can include generating a graphic to prompt receipt of registration details from the user. Step 615 can include generating a graphic display to prompt an instruction from the user of a selection of one of a series or list of predefined procedures on a series or list of predefined medical devices for the system to simulate to the user. Step 620 can include initiating the start of simulation of the selected procedure. Step 620 can include recalling or uploading the computer readable program file for the selected procedure from storage in a database or memory of the system 100.

Step 625 can include generating a graphic to prompt an instruction from the user for a desired selection from a list of modes of simulation of the procedure by the system 100. An example different the list of modes can include a watch mode and a guided mode. With the system 100, the user can learn by employing four modes of instructional delivery. The first mode can be entitled the "demonstration" mode and is used to introduce the user as to how to perform the task correctly—not requiring user participation. The simulation can run independently and allow the user to view correct tools, processes and outcomes. The second mode can be entitled the "guided" mode and can allow the user to perform the task with the aid of visual clues and hints. The third mode can be entitled the "semi-guided" mode and can allow the user to perform the task with visual hints available but only provided upon user request. The fourth mode can be entitled the "assessment" mode. In this mode, no clues or hints may be available to the user. In the assessment mode, the user can perform the task as if at an actual location of the medical device 110 and can be accessed for completion with reports being provided for instructor review and evaluation at the IOS 130.

The four modes of the system 100 can be complementary in providing the learning experience to the user. For example, the desire for the watch mode can be to observe the selected procedure prior to selection of the guided mode. In such example, the user or the instructor may desire operation of the system 100 in the watch mode for the user to first visualize the technical skills to perform the desired tasks of a simulation of a procedure in-place or the risk in allowing the user practice actions on the actual medical device 110.

In response to receipt of instruction for the watch mode, step 630 can include the system 100 generating a series of plurality of graphics visually illustrative of gestures relative to respective graphic icons or illustrations for example, refer to FIGS. 2-4) for viewing on the interactive touchscreen 135 by the user so as to observe and remember to complete tasks of procedure with respect to the actual medical device 110.

In response to receiving the instruction for selection of the semi-guided mode, step 640 can include initiating the semi-guided mode. Step 645 can include the system 100 generating displays of graphic representation or visual illustrations of each of the steps, associated tools, and gestures to perform at the touchscreen 135 for the system to detect completion by the user of the selected procedure. Step 650 can include tracking the performance of the user in completing the procedure. An example of step 650 can includes detecting and tracking a type and number of gestures by the user at the touchscreen 135, the correctness of the location and sequence of the gestures 135 relative to the location of the graphic icons as predefined for each procedure. More specifically, step 650 can include comparing a detection of the gesture by the user at the touchscreen 135 relative to a graphic representation of a virtual view of the component of the medical device 110 relative to one of a plurality of predefined tasks associated with a maintenance procedure of the medical device 110 as stored at the system 100. Step 650 to initiate tracking of predefined tasks of the selected one of the plurality of maintenance processes to the medical device can be further restricted until receiving an instruction to the IOS 130 by the instructor.

Figure 6:
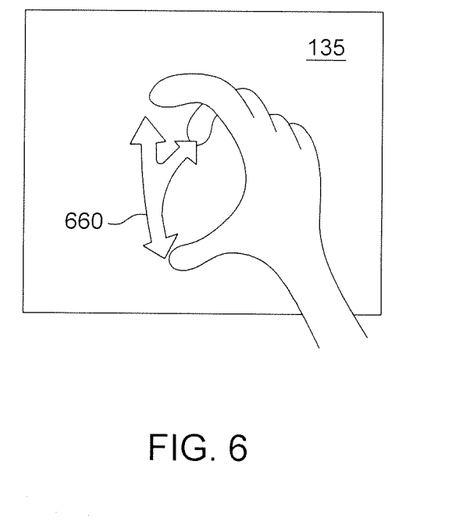
FIG. 6 shows a schematic diagram of an example gesture by a user programmed for detection by the system in accordance to the subject matter described herein.
Figure 7:
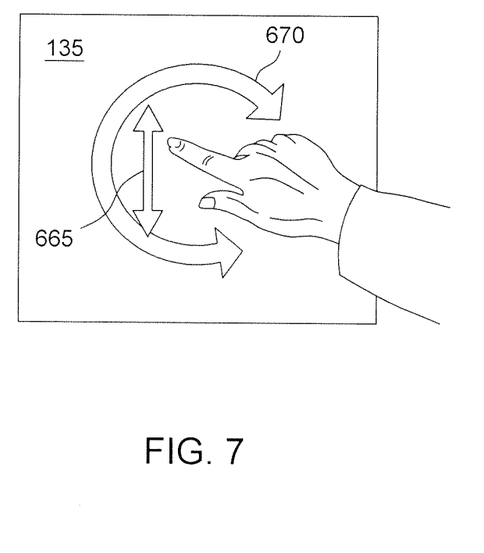
FIG. 7 shows a schematic diagram of another example gesture by a user programmed for detection by the system in accordance to the subject matter described herein.

Referring to FIGS. 6 and 7, examples of gestures programmed as computer readable instructions to be detected and recognized or identified by the system 100. FIG. 6 shows a first example gesture (shown by reference to arrow 660) can include multiple, generally simultaneous contact by the user's hand in a general a pinch movement that includes a first contact of the user finger simultaneous and different from a second contact of another user finger in a direction toward one another against the touchscreen 135, or vice versa to initiate the reverse respective action. Such gesture may be required to expand or contract a view of portions of the displays 200, 300, 400, or to grasp a component shown in such displays 200, 300, 400. The system 100 can detect and identify the occurrence of the correct type of gesture from a series thereof, but also can detect and identify if the gesture occurs at the location of the correct graphic representation, graphic icon, or visual illustration or the like of the one of the plurality of components of the medical device 110 as displayed on the touchscreen 135 (for example, see FIGS. 2-4). FIG. 7 shows other types of gestures (shown by reference to arrows 665 and 670) that the system 100 can be programmed to recognize or identify include detecting the contact and direction (e.g., up and down, curvilinear, etc.) of a user fingertip at the touch screen 135 relative to the predefined graphic representation illustrated on the touchscreen 135 of one of the plurality of components of the medical device 110 per the predefined maintenance procedure.

Step 675 can include interrupting the simulation operation of the system 100 to the user in response to detecting a user performance outside a predefined threshold. An example of step 675 can include comparing a number of user gestures detected at the touchscreen 135 to a threshold; preventing further use of the system 100 by the user in response to detecting an exceedance of the threshold. In a like manner under the assessment mode, step 680 to initiate assessment, step 685 to tracking performance, and step 690 to interrupt the simulation are analogous the steps 640, 645, 650 and 675 described above.

Step 695 can include generating a graphic or visual representation or illustration at the instructor monitor 540 located at the IOS 130 in response to detecting exceedance of the threshold, and preventing further progression through the predefined procedure until receiving an input instruction via the IOS 130 operative to allow the user to continue. Step 700 can include generating a prompt (e.g., a graphic or visual illustration) at the IOS 130 to the instructor to instruct the system 100 to either allow the user to continue through the simulation for the respective simulation procedure and the steps of tracking gestures. If the system 100 receives an instruction to allow the user to continue, then the system 100 can allow the simulation to continue. If the instructor does not input the instruction, then the system 100 can be programmed to end the simulation.

Step 705 can include the system 100 detecting completion of each of the tasks associated with the performance of the selected procedure or protocol. Step 710 can include generating an output report of a level of performance in completing each task by the user for later audits to support tracking of proper level of training of the user to perform maintenance or service on actual medical devices 110. The output report can be in the form of a digital certificate of training, etc.

Technical effects of the subject matter described above can include, but is not limited to, providing the system 100 that can be portable such that requires minimal site support infrastructure. Instructors can be able to teach a class of instruction from a centralized location to users across the world with local access to STS 120 at their remote locations. The system 100 can be reconfigured to support maintenances tasks to be performed on any type of actual medical device 110. The system 100 can substitute for practice on the actual medical devices 100, providing greater access to learning opportunities at a low cost for remote and geographically distributed user. The system 100 provides the ability to extend access to high quality training to emerging global regions which currently lack access to expensive training equipment and infrastructure or the actual medical devices 110.

Utilizing task analysis, the system 100 provides specific visibility of the user performance in regard to completing tasks correctly, in proper sequence, and in a timely manner while in a controlled environment, thereby not jeopardizing need for actual medical devices 110. Also, users have the ability to perform the tasks as many times as possible without harming or destroying the medical device. Furthermore, various troubleshooting scenarios can be simulated to the user that could otherwise not be assigned because would require damage to actual medical devices 110 in order to achieve the level of the troubleshoot. The system 100 also provides an assessment mode that can provide the opportunity to train on "virtual" medical devices 100 with exceptional realism and effectiveness without the associated cost, installation complexity and life cycle costs of parts and labor associated with training on actual medicals devices 110.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A system to virtually simulate maintenance of a medical device located in a defined space by a user, the system comprising:
   a main interactive touchscreen;
   a central controller connected in communication with the touchscreen monitor, wherein the central controller executes a plurality of computer-readable program instructions to perform:
   comparing a detection of contact by the user at the touchscreen relative to a graphic representation of a virtual view of the component of the medical device relative to one of a plurality of predefined tasks associated with a maintenance procedure of the medical device stored in a database,
   providing guidance to the user through visual cues in the event the correctness of the location and sequence of gestures of the predefined tasks is not performed correctly in response to detecting exceedance of a threshold; and
   generating a display illustrative of a completion of the maintenance procedure upon calculating a completion of each of the plurality of predefined tasks.

2. The system of claim 1, wherein the central controller includes a non-transitory programmable memory to store the plurality of computer-readable programming instructions for execution by a computer processor to perform:
   generating a first graphic representation on the touchscreen illustrative of a virtual view of the actual medical device relative to a virtual view of the defined space; and
   generating a plurality of graphic representations on the touchscreen each associated with predefined viewpoints of the medical device relative to the defined space, for selection by the user.

3. The system of claim 1, wherein the central controller includes a non-transitory programmable memory that stores the plurality of computer-readable programming instructions for execution by a computer processor to perform:
   generating a plurality of second visual graphic representations associated with a virtual image of each of a plurality of predefined components of the medical device predetermined to be visualized at the predefined viewpoints of the medical device, generated in response to a user instruction of selection at the touchscreen of one of the plurality of graphic representations associated with predefined virtual viewpoints of the medical device.

4. The system of claim 1, wherein the central controller includes a non-transitory programmable memory that stores the plurality of computer-readable programming instructions for execution by a computer processor to perform:
   detecting a gesture by the user at the touchscreen relative to the second visual graphic representations of each of the plurality of predefined components of the medical device.

5. The system of claim 1, wherein the central controller includes a non-transitory programmable memory that stores the plurality of computer-readable programming instructions for execution by a computer processor to perform:
   receiving an instruction to track completion of a maintenance procedure having a sequence of a plurality of predefined tasks to be virtually performed on the medical device.

6. The system of claim 1, wherein the central controller includes a non-transitory programmable memory that stores the plurality of computer-readable programming instructions for execution by a computer processor to perform:
   comparing the location and direction of physical gesture detected at the touchscreen relative in determining a completion of one of the plurality of predefined tasks of the maintenance procedure to be virtually performed on the medical device in determining; and
   generating the graphic display illustrative of a completion of the one of the plurality of predefined tasks dependent on the comparing step.

7. The system of claim 2, wherein the plurality of predefined virtual views of the medical device includes a rear view opposite a front view of the medical device, and a first side view opposite a second side view of the medical device.

8. The system of claim 2, wherein one of the plurality of predefined virtual views of the medical device includes a graphic illustration of at least one component not shown in another of the predefined virtual views of the medical device.

9. The system of claim 2, wherein the system generates a graphic display illustrative of the completion of one of the plurality of predefined tasks in response to detecting a predefined user gesture at the touchscreen relative to the graphic illustration of one of the plurality of components of the medical device shown on the touchscreen monitor.

10. The system of claim 2, wherein the plurality of steps further includes:
    generating a visual illustration of a predefined set of tools associated with completing the respective maintenance process on the medical device, wherein the comparing step further includes comparing a selection of one of the predefined set of tools per interaction by the user at the visual illustration on the touchscreen relative to the one of the plurality of stored maintenance processes to the medical device.

11. The system of claim 2, wherein at least one of the stored maintenance files stored on the system includes information of a predefined tool to complete a predefined task step in providing maintenance to the medical device.

12. The system of claim 2, wherein the system further includes a control console of the medical device in communication the controller.

13. The system of claim 2, wherein the system further includes an instructor workstation in communication over a network with the touchscreen, wherein the instruction workstation includes program instructions for execution by the computer processor to:
    initiate tracking completion of predefined tasks of the selected one of the plurality of maintenance processes to the medical device in response to an input to the instruction workstation by an instructor.

14. The system of claim 9, further including programming instructions for execution by the computer processor to perform the steps of:
    comparing a number of user gestures detected at the touchscreen to a threshold;
    preventing further use of the system by the user in response to detecting exceedance of the threshold.

15. The system of claim 2, further including programming instructions for execution by the computer processor in performing the steps of:
    generating a graphic visualization at an instruction monitor located at the instructor workstation in response to detecting exceedance of the threshold, and
    preventing further progression through the predefined procedure until receiving an input instruction via the instructor workstation operative to allow the user to continue.

16. The system of claim 2, wherein the predefined user gestures is a predefined movement in a predefined direction of the one of the plurality of predefined components of the medical device.

17. The system of claim 1, wherein the detecting the contact at the touchscreen is detecting a pinch movement that includes a first contact of the user finger simultaneous and different from a second contact of another user finger in a direction toward one another at the graphic representation of the one of the plurality of components of the medical device on the touchscreen.

18. The system of claim 1, wherein detecting the contact at the touch screen includes detecting a finger of the user at the graphic representation of one of the plurality of components of the medical device on the touchscreen.

19. The system of claim 1, further including a control panel of the medical device connected in communication with the central controller.

20. A method to virtually simulate maintenance of a medical device located in a defined space by a user, the method comprising the steps of:
    generating a graphic image by computer processor at a touchscreen representative of a component of the medical device;
    comparing a detection of contact by the user at the touchscreen relative to the graphic representation of a virtual view of the component of the medical device relative to one of a plurality of predefined tasks associated with a maintenance procedure of the medical device as stored in a database,
    providing guidance to the user through visual cues in the event the correctness of the location and sequence of gestures of the predefined tasks is not performed correctly in response to detecting exceedance of a threshold; and
    generating an output in electronic format illustrative of a completion of the maintenance procedure upon calculating a completion of each of the plurality of predefined tasks.

* * * * *